United States Patent [19]

Moewius et al.

[11] Patent Number: 4,767,458
[45] Date of Patent: Aug. 30, 1988

[54] WOOD PRESERVATIVE COMPOSITION AND USE THEREOF

[75] Inventors: Frank Moewius; Manfred Meisel; Herbert Grunze; Lothar Kolditz, all of Berlin; Marina Zeibig, Wernsdorf; Walfried Oese; Dietmar Standfuss, both of Dohna: Horst Kirk, Eberswalde-Finow; Reiner Hesse, Eberswalde-Finow; Horst Goetze, Eberswalde-Finow; Wibke Unger, Eberswalde-Finow, all of German Democratic Rep.

[73] Assignee: Desowag Materialschutz GmbH, Duesseldorf, Fed. Rep. of Germany

[21] Appl. No.: 96,492

[22] Filed: Sep. 15, 1987

[30] Foreign Application Priority Data

Sep. 15, 1986 [DD] German Democratic Rep. ... 294408
Dec. 5, 1986 [DD] German Democratic Rep. ... 297085

[51] Int. Cl.⁴ .......................... C09D 5/14; B05D 7/06; B27K 3/32; A01N 59/26
[52] U.S. Cl. .............................. 106/18.31; 106/18.32; 106/18.35; 106/14.12; 424/128; 424/140; 424/151; 424/160; 427/297; 427/440; 428/541
[58] Field of Search ............... 106/14.12, 18.31, 18.32, 106/18.35, 18.36; 424/128, 140, 144, 147, 151, 160; 427/297, 440; 428/541; 423/301, 306

[56] References Cited

U.S. PATENT DOCUMENTS

| | | | |
|---|---|---|---|
| 3,247,059 | 4/1966 | Bauer | 424/166 |
| 3,769,387 | 10/1973 | Wiesboeck et al. | 423/301 |
| 4,132,572 | 1/1979 | Parant et al. | 106/14.12 |
| 4,613,450 | 9/1986 | Moran et al. | 106/14.12 |

FOREIGN PATENT DOCUMENTS

| | | | |
|---|---|---|---|
| 491638 | 3/1976 | Australia | 424/140 |
| 1492509 | 5/1969 | Fed. Rep. of Germany | |
| 2202448 | 8/1972 | Fed. Rep. of Germany | |
| 2418859 | 11/1974 | Fed. Rep. of Germany | |
| 3032463 | 4/1982 | Fed. Rep. of Germany | |
| 3336557 | 4/1985 | Fed. Rep. of Germany | |
| 2095113 | 9/1982 | United Kingdom | 424/128 |
| 954228 | 9/1982 | U.S.S.R. | 424/140 |

OTHER PUBLICATIONS

Prof. Dr. Ernst Bartholome et al., "Ullmann Encyclopedia of Industrial Chemistry", Wood Protection, 4th Edition, vol. 12, pp. 685–687, Weinheim 1976.

*Primary Examiner*—Paul Lieberman
*Assistant Examiner*—Helene Kirschner
*Attorney, Agent, or Firm*—Foley & Lardner, Schwartz, Jeffery, Schwaab, Mack, Blumenthal & Evans

[57] ABSTRACT

A wood preservative based on leaching-resistant, inorganic compounds for protection of wood and wood materials against wood-damaging insects and fungi, including wood-rot fungi, is disclosed. The wood preservative, which is fixed without chromium, contains as active ingredient in an aqueous solution which is stable on impregnation, (a) a Cu(II), Zn, Ni, Co, Fe, Mg and/or Mn salt of monofluorophosphoric acid, or (b) an alkali metal salt and/or ammonium salt of monofluorophosphoric acid, in the presence of a Zn, Ni, Co, Fe, Mg and/or Mn salt of hydrochloric, nitric or sulfuric acid and, optionally in addition to (a) or (b), one or more members of the group comprising $NH_3$, HCl, $HNO_3$, $H_2SO_4$, HF, alkali metal hydrogen fluoride and ammonium hydrogen fluoride. Alternately, the composition contains (c) an alkali metal salt and/or ammonium salt of monofluorophosphoric acid in the presence of a Cu(II) salt of hydrochloric, nitric or sulfuric acid in a $Cu^{2+}:PO_3F^{2-}$ ratio of from about 0.5 to 2:1, preferably about 1:1, and, in addition, ammonia, hydrochloric acid, nitric acid, sulfuric acid or hydrofluoric acid, or alkali metal hydrogen fluoride or ammonium hydrogen fluoride.

19 Claims, No Drawings

WOOD PRESERVATIVE COMPOSITION AND USE THEREOF

BACKGROUND OF THE INVENTION

The present invention relates to a wood preservative composition based on leaching-resistant, inorganic compounds for protection of lumber, irrespective of the moisture content, against wood-damaging insects and fungi, including wood rot fungi (soft wood fungi). The lumber to be protected can be used in covered areas and also in the open, at ground level and/or exposed where constantly subjected to weathering.

Numerous inorganic wood preservatives are already known for protection of wood against damage by insects and/or fungi. Processes for introducing the preservatives into the wood are likewise known, for example, open tank, pressure, paste, spray or brush-coating processes.

Known "classical" wood preservatives based on inorganic compounds are mixtures of chromium and fluorine compounds, the so-called CF salts (see also ULLMANN's Encyklopädie der technischen Chemie [ULLMAN's Encyclopedia of Industrial Chemistry], 4th edition, volume 12, Verlag Chemie, Weinheim 1976, reference Wood Protection, p. 685).

In order to increase the insecticidal action of such agents, arsenic compounds, which are highly toxic to warm-blooded animals, are added (CFA salts). The protective salts mentioned are, for example, mixtures of sodium fluoride and potassium dichromate, optionally with potassium arsenate or sodium arsenate. Readily soluble protective salt mixtures additionally contain potassium hydrogen fluoride.

In these agents, the fluorine and arsenic compounds function as active ingredients against wood-damaging insects and fungi. The chromates and dichromates are neither insecticidally nor fungicidally active, but they are absolutely necessary in order to fix the fluorides in the form of alkali metal chromium fluorides (chromium cryolites) or the arsenates as chromium arsenates. The result is that compounds which are difficult to leach out by water are fixed in the wood in this fashion.

Furthermore, a second, equally important function, namely reduction of corrosion of iron and steel materials by the protective salt solutions, is achieved by the chromium. For fixation and corrosion reduction, considerable, fungicidally and insecticidally ineffective amounts of chromium must be used.

Although the inorganic wood-protection salt mixtures mentioned above are able to protect against damage by a very wide variety of wood-damaging insects and fungi, they provide no protection against wood-rot fungi. For this, treatment with protective salt mixtures which also contain active ingredients against wood-rot fungi is necessary. Known inorganic active ingredients of this type are, in particular, compounds of copper, but also include zinc, nickel and cobalt, and the strong toxins cadmium and mercury.

The necessary fixation in the wood of the components which are active against wood rot is likewise carried out in many known wood preservatives through chromium in the form, for example, of copper chromtes (so-called CC salts), usually together with further insecticidal and fungicidal active ingredients, such as arsenic (CCA) or boron (CCB) or fluorine (CCF salts), see also ULLMANS's Encyclopedia, supra, p. 687. A CCF-salt wood preservative based on complex silicofluorides or boron fluorides, copper salts and ammonium chromate or dichromate is described in German Auslegeschrift No. 1,492,509.

Patent specifications are also known that disclose wood preservatives which act against wood-rot fungi and are based on copper and/or zinc and contain no chromium. German Offenlegungsschrift No. 3,032,463 describes wood preservatives based on copper and/or zinc salts of weak acids, such as acetic, propionic, butyric or other acids, and German Auslegeschrift No. 2,202,448 describes preservatives based on copper, ammonia, carbon dioxide and fatty acids. German Offenlegungsschrift No. 2,418,859 describes wood preservatives based on copper or another amine-forming metal, such as zinc, cobalt or nickel, or based on amine, carbon dioxide and polyphosphates.

German Offenlengungsschrift No. 3,336,557 discloses a wood preservative based on alkali metal or ammonium monofluorophosphates, but this makes an additional component for leaching-resistant fixation in the wood necessary.

SUMMARY OF THE INVENTION

It is therefore an object of the present invention to provide an improved wood preservative composition.

It is a particular object of the invention to provide a wood preservative based on inorganic compounds in aqueous solutions which contains monofluorophosphates of polyvalent metals and with which a leaching-resistant protection of lumber, irrespective of the moisture content, against wood-damaging insects and fungi, including wood-rot fungi, is achieved without the use of chromium compounds.

A further object of the invention is to provide a wood preservative composition that results in reduction of corrosion of iron materials.

It is also an object of the invention to provide such a composition which, in addition, is considerably cheaper.

Still another object of the invention is to provide a method of treating wood using the composition according to the invention.

It is also an object of the invention to provide treated wood products using the compositions of the invention.

In accomplishing the foregoing objects, there has been provided according to one aspect of the invention a wood preservative composition for protection of wood and wood materials against wood-damaging insects and fungi, including wood-rot fungi, comprising an aqueous solution of an active ingredient selected from (A) a copper(II), zinc, nickel, cobalt, iron, magnesium and/or manganese salt of monofluorophosphoric acid $H_2PO_3F$; or (B) an alkali metal salt and/or ammonium salt of monofluorophosphoric acid in the presence of a zinc, nickel, cobalt, iron, magnesium and/or manganese salt of hydrochloric, nitric or sulfuric acid; or (C) an alkali metal salt and/or ammonium salt of monofluorophosphoric acid in the presence of a Cu(II) salt of hydrochloric, nitric or sulfuric acid in a $Cu^{2+}:PO_3F^{2-}$ ratio of from about 0.5 to 2:1, and one or more members of the group comprising ammonia, hydrochloric acid, nitric acid, sulfuric acid, hydrofluoric acid, alkali metal hydrogen fluoride and ammonium hydrogen fluoride. Where the active ingredient comprises (A) or (B), the composition preferably further comprises one or more members of the group comprising ammonia, hydrochloric acid, nitric acid, sulfuric acid, hydrofluoric acid, alkali metal hydrogen fluoride and ammonium hydrogen fluoride.

In accordance with another aspect of the invention, there has been provided a method of treating wood against wood-damaging insects and fungi, including wood-rot fungi, comprising the step of applying to wood a wood-preserving amount of a wood preservative composition as defined above.

In accordance with another aspect of the invention, there has been provided a treated wood article, comprising a wood article having impregnated therein a wood preservative residue of a composition defined above, the residue being fixed to the wood in a manner resistant to leaching by water.

Finally, the invention provides, according to still another aspect, a mixed crystal compound of the formula $(Cu_{2-m}Zn_m)K(OH)(PO_3F)_2 \cdot H_2O$, which is prepared by starting from a $Cu_2K(OH)(PO_3F)_2 \cdot H_2O$ host lattice, and the copper is partly substituted by zinc, and wherein $0 < m < 1$.

Further objects, features and advantages of the present invention will become apparent from the detailed description of preferred embodiments which follows.

DETAILED DESCRIPTION OF THE PREFERRED EMBODIMENTS

A wood preservative based in inorganic compounds for protection of lumber, irrespective of the moisture content, against wood-damaging insects and fungi, including wood-rot fungi, has been found. The active component contained in this wood preservative is:

(a) a copper(II), zinc, nickel, cobalt, iron, magnesium and/or manganese salt of monofluorophosphoric acid $H_2PO_3F$, or (b) an alkali metal salt and/or ammonium salt of monofluorophosphoric acid, in the presence of a zinc, nickel, cobalt, iron, magnesium and/or manganese salt of hydrochloric, nitric or sulfuric acid, and additionally, if desired for increasing the solubility of the components mentioned under (a) and (b), ammonia, hydrochloric acid, nitric acid, sulfuric acid or hydrofluoric acid, or alkali metal hydrogen fluoride or ammonium hdrogen fluoride, so that the active component is always present in an aqueous solution which is stable on impregnation.

According to the invention, the wood preservative can also contain as an active ingredient:

(c) an alkali metal salt and/or ammonium salt of monofluorophosphoric acid in the presence of a Cu(II) salt of hydrochloric, nitric or sulfuric acid in a $Cu^{2+}:PO_3F^{2-}$ ratio of from about 0.5 to 2:1, preferably from about 1:1, and in addition one or more members of the group comprising ammonia, hydrochloric acid, nitric acid, sulfuric acid, hydrofluoric acid, alkali metal hydrogen fluoride and ammonium hydrogen fluoride, so that the active component is present in an aqueous solution which is stable on impregnation.

The cadmium salt would also be an effective metal salt for use in the present invention, but, overall, it is not preferable due to its polluting action.

The wood preservative can preferably contain as the metal salt three-component mixtures of a Cu, Zn and Mn salt, a Cu, Zn and Mg salt, a Mn, Zn and Mg salt, or a Co, Ni and Zn salt;

two-component mixtures of a Cu and Zn salt, a Cu and Mg salt, a Zn and Mg salt, or an Mn and Zn salt, optionally in the presence of an alkali metal salt of monofluorophosphoric acid and/or an ammonium salt of monofluorophosphoric acid; and a Cu or Zn or Ni or Co salt.

Furthermore, the composition can preferably contain as the alkali metal salt on Na or K salt.

Furthermore, the compositions of the invention can preferably contain as the active ingredient an ammonium salt of monofluorophosphoric acid in the presence of a Cu, Zn, Ni, Co, Fe, Mg and/or Mn salt of hydrochloric, nitric or sulfuric acid, or a potassium salt of monofluorophosphoric acid in the presence of a Cu salt of hydrochloric or sulfuric acid.

In order to increase the solubility of the active ingredient, the acid used is preferably hydrochloric or sulfuric acid. Cu, Zn, Ni, Co, Fe, Mg and Mn salts of monofluorophosphoric acid means the individual salts of this acid alongside one another as well as double salts of two or more cations.

The Cu(II) salts of monofluorophosphoric acid mentioned under (a) also include those such as Cu-K monofluorophosphate.

Particularly preferred wood preservatives according to the invention in which leaching-resistant fixation is possible without addition of chromium are those which contain as active ingredients copper ($Cu^{2+}$) ions and zinc ($Zn^{2+}$) ions and monofluorophosphate ($PO_3F^{2-}$) ions in a $(Cu^{2+}+Zn^{2+}):PO_3F^{2-}$ ratio of about 0.5 to 2:1, preferably about 1:1, and in a $Zn^{2+}:Cu^{2+}$ ratio of about 10 to 60:90 to 40, preferably about 20 to 50:80 to 50, and which, in addition, contain one or more members of the group comprising ammonia, hydrochloric acid, nitric acid, sulfuric acid, hydrofluoric acid, alkali metal hydrogen fluoride and ammonium hydrogen fluoride.

Of the particularly preferred wood preservatives, the most preferred is one which contains as active ingredient the compounds potassium dicopper hydroxide bis(monofluorophosphate) monohydrate $Cu_2K(OH)(PO_3F)_2 \cdot H_2O$ and zinc monofluorophosphate 2.5-hydrate $ZnPO_3F \cdot 5/2H_2O$.

It can also preferably contain the novel mixed-crystal compound $(Cu_{2-m}Zn_m)K(OH)(PO_3F)_2 \cdot H_2O$ in which, starting from the $Cu_2K(OH)(PO_3F)_2 \cdot H_2O$ host crystal lattice, the copper is partly substituted by zinc, and where m is less than one and greater than zero.

The content of the active ingredient copper(II), zinc, nickel, cobalt, iron, magnesium and/or manganese salt of monofluorophosphoric acid can be between about 0.5 and 20% by weight, preferably between about 2 and 15% by weight, in particular between about 2 and 8% by weight, and that of the active ingredient alkali metal salt and/or ammonium salt of monofluorophosphoric acid and copper(II), zinc, nickel, cobalt, iron, magnesium and/or manganese salt of hydrochloric, nitric or sulfuric acid can be between about 1 and 30% by weight, preferably between about 2 and 15% by weight.

The aqueous solution of the agent can additionally contain between about 0.5 and 10% by weight, preferably between about 1 and 5% by weight, in particular between about 1.0 and 3% by weight, of ammonia, hydrochloric acid, nitric acid, sulfuric acid or hydrofluoric acid, or alkali metal hydrogen fluoride or ammonium hydrogen fluoride.

The active ingredients according to the invention are obtained in a known fashion. The above-mentioned crystalline, basic copper potassium monofluoromonophosphate of the formula $Cu_2K(OH)(PO_3F)_2.H_2O$ is obtained in an industrially simple fashion or secondary salt of this acid is reacted with a copper(II) salt in the presence of potassium ions. The reaction is carried out in an aqueous medium at a reaction temperature of, preferably, from about 5° to 35° C., in particular from about 15° to 25° C., preferably with addition of a base, such as potassium hydroxide.

Basic copper potassium monofluoromonophosphate is thus preferably obtained when potassium monofluoromonophosphate $K_2PO_3F$ is reacted with water-soluble copper salts, such as copper chloride or nitrate or sulfate, in water, for example in the $PO_3F^{2-}:Cu^{2+}$ molar ratio of about 1:1. The desired compound is sparingly soluble in water and therefore precipitates on addition of the first starting solution to the other.

However, basic copper potassium monofluoromonophosphate can also be obtained by reaction of sodium monofluoromonophosphate or ammonium monofluoromonophosphate with water-soluble copper salts, such as copper chloride, nitrate or sulfate, in the presence of soluble potassium salts, such as, for example, potassium chloride, nitrate or sulfate.

If monofluoromonophosphates of alkaline-earth metals, lead or, for example, silver are reacted with copper salts in the presence of potassium salts, basic copper potassium monofluoromonophosphate can likewise be isolated. Basic copper potassium monofluoromonophosphate can also be prepared using monofluoromonophosphoric acid. In this case, copper carbonate, hydroxide or oxide or basic copper carbonate is preferably employed as the copper salt, and the reaction is carried out in the presence of a soluble potassium salt and, optionally, with addition of a base, preferably potassium hydroxide. Finally, it has been found that basic copper potassium monofluoromonophosphate is also obtained by reaction of the starting components monofluoromonophosphoric acid or a primary or secondary salt of this acid with a copper salt in the presence of potassium ions in an inorganic solvent when at least one of the starting compounds is soluble in this solvent and stoichiometric amounts of water are present, for example, from a copper salt hydrate. Thus, the desired compound can be prepared, for example, by reaction of potassium monofluoromonophosphate with $Cu(NO_3)_2.3H_2O$ in methanol at a reaction temperature of from about 20° C. to 65° C., preferably from about 50° C. to 65° C.

The preferred novel mixed-crystal compound $(Cu_{2-m},Zn_m)K(OH)(PO_3F)_2.H_2O$ according to the invention can be obtained by reacting monofluorophosphoric acid $H_2PO_3F$ or primary or secondary salts of this acid with a copper(II) and zinc salt in the presence of potassium ions in aqueous solution. It is preferably prepared by reacting potassium monofluorophosphate $K_2PO_3F$ with water-soluble copper and zinc salts, such as the chlorides, nitrates or sulfates. This mixed-crystal compound crystallizes in the crystal structure of the pure copper compound $Cu_2K(OH)(PO_3F)_2.H2O$. The proportion of zinc m which is substituted by copper, where $0<m<1$, i.e., wherein the ratio approaches 50 ml-%, is dependent on the $Cu^{2+}:Zn^{2+}$ ratio in the precipitation solution.

Although simple inorganic compounds such as, for example, sodium fluoride and copper(II) sulfate have the essential fungicidal effectiveness (see Table 1), they are, however, easily leached out of the wood (e.g. 82% of the copper sulfate introduced, see ULLMANN's Encyclopedia, supra, p. 689).

Surprisingly, it has been found that copper(II), zinc, nickel, cobalt, iron, magnesium and/or manganese salts of monofluorophosphoric acid $H_2PO_3F$ are fixed in leaching-resistant manner after introduction into the wood and that a composition containing one or more of the these compounds effectively protects lumber against damage by wood-damaging insects and fungi, including wood-rot fungi (see Table 1 for the threshold values of the antifungal activity of known wood preservatives and those according to the invention).

It has furthermore been found that mixtures of alkali metal monofluorophosphates and/or ammonium monofluorophosphates with soluble salts of the metals mentioned can be used in place of monofluorophosphates of these metals. These mixtures have biocidal activities and fixation behaviors like the monofluorophosphates of polyvalent metals. It should be particularly emphasized that the wood preservatives according to the invention are fixed in the wood without addition of chromium.

As comparison of the fungicidal threshold values for NaF or, for example, $CuSO_4.5H_2O$ with those of the wood preservatives according to the invention shows, the application rates relative to the component fluorine which is active against Basidiomycetes or the component, for example, copper and zinc, which is active against wood-rot fungi is in some cases considerably reduced when the wood preservatives according to the invention are used (Table 2). This is the consequence of a synergistic effect of the P-F bond in the monofluorophosphate or the complex bond of, for example, copper or zinc in the monofluorophosphate. However, a further synergistic effect obviously occurs in addition in the preferred Cu-Zn-K monofluorophosphate combinations since the individual action of the Cu-K monofluorophosphate and of the Zn monofluorophosphate, although very good in each case, are not as good as those of the Cu-Zn-K combination.

The wood preservatives are ecologically acceptable; with the exception of the ammonia-containing ones, they are odorless. The solutions have a good penetration capability into the wood, and the magnesium and zinc salts leave the wood colorless. If metals are used which form colored complex salts, slight discoloration of the impregnated wood takes place. The wood preservatives according to the invention are suitable for impregnation of wood for varying moisture content and are suitable both for initial and subsequent protection.

The corrosion behavior of ammoniacal wood-preservative solutions towards iron metals is non-corrosive or weakly corrosive. In contrast, neutral and acidic copper salt solutions naturally dissolve iron. As expected, hydrogen fluoride-containing solutions corrode iron materials to a very large extent. The corrosion behavior towards copper materials is reversed; whereas ammoniacal solutions cause dissolution of the copper, neutral and acidic or hydrogen fluoride-containing solutions corrode copper moderately.

Finally, the wood preservatives according to the invention are also active against termites. The activity depends on the concentration. Thus, for example, 80% of worker termites and 90% of their intestinal symbionts are killed by use of a 5% strength by weight solution of the active ingredient $Cu_2K(OH)(PO_3F)_2 \cdot H_2O$ in ammonia solution after an experimental duration of 14 days, and relative loss in weight of the test samples cannot be measured, merely very slight damage being visually detectable.

Particularly favorable results are achieved with the wood preservatives according to the invention which contain as the active ingredient Cu, Zn and monofluorophosphate ions in a $(Cu^{2+} + Zn^{2+}):PO_3F^{2-}$ ratio of from about 0.5 to 2:1 in the form already shown above. The activity (after water leaching) of the agents against wood-rot fungi, such as *Chaetomium globosum*, is less than 1 kg of water preservative/m$^3$ of wood and against Basidiomycetes, such as *Coniophora puteana*, around 3 kg/m$^3$, and they are fixed in a leaching-resistant fashion and cause no pollutant.

In aqueous solution, the wood preservatives according to the invention may contain further ingredients, such as, for example, known biocidal compounds, wetting agents, dyestuffs and similar substances.

The invention will be described below in greater detail by means of non-limiting, illustrative examples. Examples of wood preservatives formulated according to the invention are given below (% data are in % by weight):

EXAMPLE 1

First, 6.0 g of concentrated ammonia (25% strength) are introduced into 94.0 g of water and then 3.0 g of $Cu_2K(OH)(PO_3F)_2 \cdot H_2O$ (product which is obtainable according to Example 33) are dissolved. The solution is then ready for use.

In the further examples, the following components are likewise added to water in the sequence given and dissolved:

EXAMPLE 2

98.0 g of water
2.0 g of conc. $H_2SO_4$
3.0 g of $Cu_2K(OH)(PO_3F)_2 \cdot H_2O$.

EXAMPLE 3

100.0 g of water
2.0 g of $NaHF_2$
1.0 g of $Cu_2K(OH)(PO_3F)_2 \cdot H_2O$.

EXAMPLE 4

90.0 g of water
10.0 g of conc. ammonia
3.75 g of $CuSO_4 \cdot 5H_2O$
2.64 g of $K_2PO_3F$.

EXAMPLE 5

95.0 g of water
2.58 g of $NH_4HF_2$
3.75 g of $CuSO_4 \cdot 5H_2O$
2.64 g of $K_2PO_3F$.

EXAMPLE 6

100.0 g of water
3.0 g of conc. HCl
2.56 g of $CuCl_2 \cdot 2H_2O$
2.16 g of $Na_2PO_3F$.

EXAMPLE 7

100.0 g of water
1.0 g of conc. $H_2SO_4$
3.75 g of $CuSO_4 \cdot 5H_2O$
2.01 g of $(NH_4)_2PO_3F$.

EXAMPLE 8

92.0 g of water
8.0 g of conc. ammonia
3.75 g of $CuSO_4 \cdot 5H_2O$
2.01 g of $(NH_4)_2PO_3F$.

EXAMPLE 9

92.0 g of water
8.0 g conc. ammonia
3.0 g of $ZnPO_3F \cdot 2.5H_2O$.

EXAMPLE 10

100.0 g of water
0.5 g of $KHF_2$
2.0 g of $ZnPO_3F \cdot 2.5H_2O$.

EXAMPLE 11

94.0 g of water
6.0 g of conc. ammonia
3.0 g of $(Cu_{1.44}Zn_{0.57})K(OH)(PO_3F)_2 \cdot H_2O$ (product which is obtainable according to Example 35).

EXAMPLE 12

94.0 g of water
6.0 g of conc. ammonia
0.63 g of $ZnPO_3F \cdot 2.5H_2O$
2.38 g of $Cu_2K(OH)(PO_3F)_2 \cdot H_2O$.

EXAMPLE 13

92.0 g of water
8.0 g of conc. ammonia
1.56 g of $ZnPO_3F \cdot 2.5H_2O$
1.50 g of $Cu_2K(OH)(PO_3F)_2 \cdot H_2O$.

EXAMPLE 14

92.0 g of water
8.0 g of conc. ammonia
2.64 g of $K_2PO_3F$
0.87 g of $ZnSO_4 \cdot 7H_2O$
3.00 g of $CuSO_4 \cdot 5H_2O$.

EXAMPLE 15

100.0 g of water
1.5 g of $KHF_2$
2.16 g of $Na_2PO_3F$
0.90 g of $Zn(NO_3)_2 \cdot 6H_2O$
2.90 g of $Cu(NO_3)_2 \cdot 3H_2O$.

EXAMPLE 16

100.0 g of water
1.50 g of conc. $H_2SO_4$
2.01 g of $(NH_4)_2PO_3F$
1.49 g of $Zn(NO_3)_2 \cdot 6H_2O$
1.70 g of $CuCl_2 \cdot 2H_2O$.

EXAMPLE 17

100.0 g of water
1.30 g of $NH_4NF_2$
2.64 g of $K_2PO_3F$
2.15 g of $ZnSO_4 \cdot 7H_2O$ 1.88 g of CuSO$_4$.5H$_2$O.

EXAMPLE 18

94.0 g of water
6.0 g of conc. ammonia
4.0 g of NiPO$_3$F.7H$_2$O.

EXAMPLE 19

90.0 g of water
10.0 g of conc. ammonia
5.0 g of CoPO$_3$F.6H$_2$O.

EXAMPLE 20

100.0 g of water
2.5 g of conc. H$_2$SO$_4$
3.0 g of MnPO$_3$F.4H$_2$O.

EXAMPLE 21

100.0 g of water
3.0 g of conc. HNO$_3$
4.0 g of Fe$_2$(PO$_3$F)$_3$.12H$_2$O.

EXAMPLE 22

100.0 g of water
3.05 g of MgCl$_2$.6H$_2$O
2.64 g of K$_2$PO$_3$F.

EXAMPLE 23

100.0 g of water
2.01 g of (NH$_4$)$_2$PO$_3$F
3.70 g of MgSO$_4$.7H$_2$O.

EXAMPLE 24

100.0 g of water
3.94 g of NiSO$_4$.6H$_2$O
2.64 g of K$_2$PO$_3$F.

EXAMPLE 25

90.0 g of water
10.0 g of conc. ammonia
2.16 g of Na$_2$PO$_3$F
4.46 g of Zn(NO$_3$)$_2$.6H$_2$O.

EXAMPLE 26

100.0 g of water
2.64 g of K$_2$PO$_3$F
3.35 g of MnSO$_4$.4H$_2$O.

EXAMPLE 27

100.0 g of water
2.64 g of K$_2$PO$_3$F
4.37 g of Co(NO$_3$)$_2$.6H$_2$O.

EXAMPLE 28

100.0 g of water
5.5 g of conc. HCl
2.16 g of Na$_2$PO$_3$F
4.17 g of FeSO$_4$.7H$_2$O.

EXAMPLE 29

90.0 g of water
10.0 g of conc. ammonia
2.0 g of NH$_4$Cl
1.0 g of ZnPO$_3$F.2.5H$_2$O
1.0 g of Mg(NH$_4$)$_2$(PO$_3$F)$_2$.2H$_2$O
1.0 g of Cu$_2$K(OH)(PO$_3$F)$_2$.H$_2$O.

EXAMPLE 30

94.0 g of water
6.0 g of conc. ammonia
2.01 g of (NH$_4$)$_2$PO$_3$F
1.50 g of Zn(NO$_3$)$_2$.6H$_2$O
1.45 g of Co(NO$_3$)$_2$.6H$_2$O
1.30 g of NiSO$_4$.6H$_2$O.

EXAMPLE 31

92.0 g of water
8.0 g of conc. ammonia
1.5 g of NH$_4$Cl
2.0 g of Cu$_2$K(OH)(PO$_3$F)$_2$.H$_2$O
1.0 g of Mg(NH$_4$)$_2$(PO$_3$F)$_2$.2H$_2$O.

EXAMPLE 32

94.0 g of water
6.0 g of conc. ammonia
1.6 g of NH$_4$Cl
1.52 g of MgCl$_2$.6H$_2$O
1.50 g of ZnPO$_3$F.2.5H$_2$O
1.32 g of K$_2$PO$_3$F.

The following example relates to the preparation of basic copper potassium monofluorophosphate Cu$_2$K(OH)(PO$_3$F)$_2$.H$_2$O.

EXAMPLE 33

A solution of 51.15 g of CuCl$_2$.2H$_2$O (0.3 mol) in 250 ml of H$_2$O is added dropwise to a solution of 52.85 g of K$_2$PO$_3$F (0.3 mol) in 250 ml of H2O. The precipitated residue is filtered off under suction, washed with water until free of chloride and dried over silica gel.

Yield: 37.83 g (63.8% of the phosphorus employed).
Analysis: Cu$_2$K(OH)(PO$_3$F)$_2$.H$_2$O, MW=397.16, Cu: 31.30 (calc. 32.00); K: 9.97 (9.85); P: 15.53 (15.60); F: 9.14 (9.57); Cl: 0.08 (0) %.

The compound crystallizes in the monoclinic space group B2/m with a=9.094 Å, b=7.755 Å, c=6.333 Å, $\alpha=\beta=90°$, $\gamma=117.55°$ and Z=2.

The following three examples are intended to illustrate the preparation of basic copper zinc potassium monofluorophosphate (Cu$_{2-m}$.Zn$_m$)K(OH)(PO$_3$F)$_2$.H$_2$O in greater detail.

EXAMPLE 34

12.3 g (70 mmol) of K$_2$PO$_3$F are dissolved in 60 ml of H$_2$O, and a solution of 8.5 g (50 mmol) of CuCl$_2$.2H$_2$O and 6.0 g (20 mmol) of Zn(NO$_3$)2.6H$_2$O in 60 ml of H$_2$O is added dropwise with stirring. The precipitate is washed with water until free of chloride and nitrate and is dried over silica gel until the weight remains constant.

Yield: 8.8 g (61.6% of the phosphorus employed).
Analysis, see after Example 36.

EXAMPLE 35

The following Example was carried out as described in Example 34:
10.6 g (60 mmol) of K$_2$PO$_3$F in 50 ml of H$_2$O,
5.1 g (30 mmol) of CuCl$_2$.2H$_2$O and
8.9 g (30 mmol) of Zn(NO$_3$)$_2$.6H$_2$O in 50 ml of H$_2$O.
Yield: 6.7 g (54.6% of the phosphorus employed).
Analysis, see after Example 36.

EXAMPLE 36

The following Example was carried out as described in Example 34:
10.6 g (60 mmol) of K$_2$PO$_3$F in 50 ml of H$_2$O, 4.3 g (25 mmol) of CuCl$_2$.2H$_2$O and
10.4 g (35 mmol) of Zn(NO$_3$)$_2$.6H$_2$O in 50 ml of H$_2$O.

Yield: 6.1 g (49.6% of the phosphorus employed).

Analysis of the products obtained according to Examples 34 to 36 by paper chromatography showed that the products comprise pure monofluorophosphate. X-ray studies showed that the three products are isotypic with the zinc-free compound Cu$_2$K(OH)(PO$_3$F)$_2$.H$_2$O. From the analytical results, the copper:zinc:phosphorus ratio and the magnitude of m in the general formula was calculated for each product, and the initial atom ratios in the precipitation solution were compared:

| Example | Cu:Zn:P ratio of the precipitation solution | Cu:Zn:P ratio of the precipitation product | (Cu$_{2-m}$·Zn$_m$)K(OH)(PO$_3$F)$_2$.H$_2$O m= |
|---|---|---|---|
| 34 | 1.43:0.57:2 | 1.75:0.26:2 | 0.26 |
| 35 | 1:1:2 | 1.44:0.57:2 | 0.57 |
| 36 | 0.83:1.17:2 | 1.29:0.70:2 | 0.70 |

TABLE 1

Threshold values for the antifungal activity in kg of wood preservative per m$^3$ of wood[1]

| Wood preservative | Coniophora puteana no leaching | Coniophora puteana after leaching | Chaetomium globosum no leaching | Chaetomium globosum after leaching |
|---|---|---|---|---|
| CCF salt type[a] | 2.8–4[b] | 10–12[b] | 5–10[c] | 6[c] |
| CuSO$_4$.5H$_2$O[a] | — | — | 4[c] | ca. 15[c] |
| NaF | 0.4–0.6 | — | — | — |
| Illustrative embodiment: | | | | |
| 1 | 0.3 | 3.4–6.5 | 0.4–0.9 | <0.3 |
| 2 | 1.0–2.0 | >10. | 0.2–0.3 | <0.3 |
| 3 | <0.2 | 8–12(10)[d] | 0.6–0.9 | <0.9 |
| 4 | <1.3 | >7 | 6.4 | 3.5–6.3 |
| 5 | <1.9 | >10 | 1.8–2.5 | 1.8–2.7 |
| 6 | 3.2 | 19 | 2.8 | 2.1 |
| 7 | >1(3) | 11–22(15) | 0.2–0.3 | <0.9 |
| 9 | >1(2) | 3.9–7.5 | 0.4–0.6 | 0.9–1.8 |
| 10 | 0.9 | 1.2 | <2.8 | <5.4 |
| 11 | — | 0.8–3.8(2.8) | — | <0.6 |

Remarks on Tables 1 and 2:
[a]Literature values from ULLMANN's Encyclopedia, supra, p. 688.
[b]Threshold values for brown-rot fungi in general.
[c]Threshold values for wood-rot fungi in general.
[d]Values in parentheses denote the trend of the threshold value.
< Threshold value is less than the value given
> Threshold value is greater than the value given
[1]The fungicidal activity was tested in accordance with standard procedure TGL 14140/01-02 "Determination of the protective action of test substances against wood-damaging fungi in Kolle flasks, laboratory test using brown- and white-rot fungi (TGL 14140/01)" or "Laboratory test using mold fungi (TGL 14140/02)."

The test process is used to determine the threshold value for the antifungal activity of test substances. The threshold value is the absorption, in kg per m$^3$ of wood, of the test substance which is just sufficient to prevent damage to the wood by fungi. The wood protection is regarded as sufficient when no test sample of a concentration series has a weight loss of more than 3%.

For closer characterization, the threshold value is determined through the two absorption weights of test substance, in kg per m$^3$ of wood, which corresponds to the lowest concentration which protects the wood and the next-lowest concentration of the series at which the wood is no longer sufficiently protected. The threshold value without leaching of the test sample and the threshold value after standardized leaching of the test sample in distilled water were determined. In order to determine the threshold value, wooden test samples are impregnated, using the full-cell process, with impregnation solutions containing stepped concentrations of test substances, and the test samples are subjected to attack by pure cultures of wood-damaging Basidiomycetes or Ascomycetes in Kolle flasks.

TABLE 2

Fungicidal threshold values from Table 1, relative to kg of active ingredient per m$^3$ of wood:

| Active ingredient: Test fungus: Wood preservative | Fluorine Coniophora puteana without leaching | Fluorine Coniophora puteana after leaching | Copper Chaetomium globosum without leaching | Copper Chaetomium globosum after leaching |
|---|---|---|---|---|
| CCF salt type[a,e] | 0.7–1.0[b] | 2.5–3.0[b] | 0.25–0.5[c] | 0.3[c] |
| CuSO$^4$.5H$_2$O[a] | — | — | 1[c] | 3.8[c] |
| NaF | 0.15–0.3 | — | — | — |
| Illustrative embodiment: | | | | |
| 1 | 0.03 | 0.3–0.6 | 0.1–0.3 | <0.1 |
| 2 | 0.1–0.2 | >1 | 0.1 | <0.1 |
| 6 | 0.1 | 0.9 | 0.45 | 0.35 |
| 7 | >0.05(0.15)[d] | 0.5–1.1(0.8) | 0.05 | <0.15 |
| 9 | >0.1(0.2) | 0.4–0.7 | 0.15–0.2[f] | 0.3–0.6 |

Remarks on Table 2:
[a] to [d]see remarks on Table 1.
[e]Converted for a CCF salt having a copper content of 5% and a fluorine content of 25%.
[f]Data for the active ingredient zinc.

TABLE 3

Corrosive action of wood preservative solutions on iron and copper materials (long-term immersion experiment)[2]:

| Wood preservative solution | Weight loss per unit surface area after 14 days [mg/cm$^2$] |
|---|---|
| Corrosion of iron: | |
| Distilled water | 1.8 |
| Illustrative embodiment: | |

TABLE 3-continued

Corrosive action of wood preservative solutions on iron and copper materials (long-term immersion experiment)[2]:

| Wood preservative solution | Weight loss per unit surface area after 14 days [mg/cm$^2$] |
| --- | --- |
| 1 | 1.3 |
| 7 | 145 (Cu deposition) |
| 8 | 0.1 |
| 9 | 1.4 |
| 10 | 21 |
| Corrosion of copper: | |
| Ammonia (2.0% strength) | 28 |
| Illustrative embodiment: | |
| 1 | 45 |
| 9 | 75 |
| 3 | 3.9 |

[2]The corrosive action on iron and copper materials was tested in a long-term immersion experiment in accordance with standard procedure TGL 18973/01. Iron and copper sheets were suspended in 0.5 liters of the wood-preservative solution and kept therein for 14 days at 20° C. The weight loss per unit surface area was then determined.

What is claimed is:

1. A wood preservative composition protection of wood and wood materials against wood-damaging insects and fungi, including wood-rot fungi, comprising:
an aqueous solution of an active ingredient selected from
(A) 0.5 to 20% by weight of a copper (II), zinc, nickel, cobalt, iron, magnesium and/or manganese salt of monofluorophosphoric acid H2PO3F; or
(B) an alkali metal salt and/or ammonium salt of monofluorophosphoric acid in the presence of a zinc, nickel, cobalt, iron, magnesium and/or manganese salt of hydrochloric, nitric or sulfuric acid; or
(C) an alkali metal salt and/or ammonium salt of monofluorophosphoric acid in the presence of a Cu(II) salt of hydrochloric, nitric or sulfuric acid in a $Cu^{2+}$:$PO_3F^{2-}$ ratio of from about 0.5 to 2:1, and one or more members of the group comprising ammonia, hydrochloric acid, nitric acid, sulfuric acid, hydrofluoric acid, alkali metal hydrogen fluoride and ammonium hydrogen fluoride the content of the active ingredient alkali metal salt and/or ammonium salt of monofluorophosphoric acid and copper (II), zinc, nickel, cobalt, iron, magnesium, and/or manganese salt of a hydrochloric, nitric or sulfuric acid being between about 1 to 30% by weight.

2. A wood preservative composition as claimed in claim 1, wherein said active ingredient comprises (A) or (B) and said composition further comprises one or more members of the group comprising ammonia, hydrochloric acid, nitric acid, sulfuric acid, hydrofluoric acid, alkali metal hydrogen fluoride and ammonium fluoride.

3. A wood preservative composition as claimed in claim 1, containing copper ($Cu^{2+}$) and zinc ($Zn^{2+}$) and monofluorophosphate ($PO_3F^{2-}$) ions in a ($Cu^{2+}$+$Zn^{2+}$):$PO_3F^{2-}$ ratio of from about 0.5 to 2:1 and in a $Zn^{2+}$:$Cu^{2+}$ ratio of from about 10 to 60:90 to 40.

4. A wood preservative composition as claimed in claim 3, wherein said ($Cu^{2+}$+$Zn^{2+}$):$PO_3F^{2-}$ ratio is about 1:1, and, said $Zn^{2+}$:$Cu^{2+}$ ratio is from about 20 to 50:80 to 50.

5. A wood preservative composition as claimed in claim 3, comprising potassium dicopper hydroxide bis(-monofluorophosphate) monohydrate $Cu_2K(OH)(PO_3F)_2 \cdot H_2O$ and zinc monofluorophosphate 2.5-hydrate $ZnPO_3F \cdot 5/2H_2O$.

6. A wood preservative composition as claimed in claim 3, comprising a mixed-crystal compound $(Cu_{2-m},Zn_m)K(OH)(PO_3F)_2 \cdot H_2O$, which is prepared by starting from a $Cu_2K(OH)(PO_3F)_2 \cdot H_2O$ host lattice, and the copper is partly substituted by zinc, and wherein $0 < m < 1$.

7. A wood preservative composition as claimed in claim 3, comprising a alkali metal salt and/or ammonium salt of monofluorophosphoric acid and a copper and zinc salt of hydrochloric, nitric and/or sulfuric acid.

8. A wood preservative composition as claimed in claim 1, wherein said metal salt comprises a Cu, Zn or Mg salt.

9. A wood preservative composition as claimed in claim 1, wherein the alkali metal salt comprises Na and K salt.

10. A wood preservative composition as claimed in claim 1, wherein said Cu, Cu-K, Cu-Zn-K, Zn, Ni, Co, Fe, Mg and/or Mn salt of monofluorophosphoric acid is present in an amount of between about 2 to 15% by weight.

11. A wood preservative composition as claimed in claim 1, wherein said Cu, Cu-K, Cu-Zn-K, Zn, Ni, Co, Fe, Mg and/or Mn salt of monofluorophosphoric acid is present in an amount of between about 2 to 8% by weight.

12. A wood preservative composition as claimed in claim 1, wherein said alkali metal salt and/or ammonium salt of monofluorophosphoric acid and copper(II), zinc, nickel, cobalt, iron, magnesium and/or manganese salt of hydrochloric, nitric or sulfuric acid is present in an amount between about 2.0 and 15.0% by weight.

13. A wood preservative composition as claimed in claim 1, further comprising between about 0.5 and 10% by weight of ammonia, hydrochloric acid, nitric acid, sulfuric acid, hydrofluoric acid, alkali metal hydrogen fluoride or ammonium hydrogen fluoride.

14. A wood preservative composition as claimed in claim 13, wherein said ammonia, hydrochloric acid, nitric acid, sulfuric acid, hydrofluoric acid, alkali metal hydrogen fluoride or ammonium hydrogen fluoride is present in an amount of from about 1 to 5% by weight.

15. A wood preservative composition as claimed in claim 13, wherein said ammonia, hydrochloric acid, nitric acid, sulfuric acid, hydrofluoric acid, alkali metal hydrogen fluoride or ammonium hydrogen fluoride is present in an amount of from about 1 to 3% by weight.

16. A method of treating wood against wood-damaging insects and fungi, including wood-rot fungi, comprising the step of applying to wood a wood-preserving amount of a wood preservative composition as defined by claim 1.

17. A treated wood article, comprising a wood article having impregnated therein a wood preservative residue of a composition defined by claim 1, said residue being fixed to said wood in a manner resistant to leaching by water.

18. A treated wood article produced by the method defined in claim 16.

19. A mixed crystal component of the formula $(Cu_{2-m},Zn_m)K(OH)(PO_3F)_2 \cdot H_2O$, which is prepared by starting from a $Cu_2K(OH)(PO_3F)_2 \cdot H_2O$ host lattice, and the copper is partly substituted by zinc, and wherein $0 < m < 1$.

* * * * *